US008821815B2

(12) United States Patent
Shioyama et al.

(10) Patent No.: US 8,821,815 B2
(45) Date of Patent: Sep. 2, 2014

(54) CELL ISOLATION INSTRUMENT

(75) Inventors: Takahiro Shioyama, Tokyo (JP); Akane Suzuki, Tokyo (JP); Teruo Okano, Tokyo (JP); Tatsuya Shimizu, Tokyo (JP); Yuji Haraguchi, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 13/542,459

(22) Filed: Jul. 5, 2012

(65) Prior Publication Data

US 2013/0028813 A1    Jan. 31, 2013

(30) Foreign Application Priority Data

Jul. 26, 2011    (JP) .................................. 2011-163166

(51) Int. Cl.
*B01D 35/00*    (2006.01)
*C12M 1/33*    (2006.01)
(52) U.S. Cl.
CPC ..................................... *C12M 45/02* (2013.01)
USPC ............... 422/534; 422/536; 422/64; 422/65; 422/66; 422/67
(58) Field of Classification Search
USPC ...................................... 422/63–67, 534, 536
See application file for complete search history.

(56) References Cited

U.S. PATENT DOCUMENTS

| 6,223,652 | B1 | 5/2001 | Calia et al. | |
| 6,830,935 | B1 * | 12/2004 | El-Amin et al. | ............... 436/177 |
| 2007/0148756 | A1 | 6/2007 | Bullen et al. | |
| 2009/0084275 | A1 | 4/2009 | Liang | |
| 2010/0112696 | A1 | 5/2010 | Min | |

FOREIGN PATENT DOCUMENTS

| GB | 796882 A | 6/1958 |
| JP | 2007-505631 A | 3/2007 |
| WO | 2005/030936 A1 | 4/2005 |

OTHER PUBLICATIONS

Extended European Search Report for the related European Patent Application No. 12177415.2 dated Nov. 7, 2012.

* cited by examiner

*Primary Examiner* — Jyoti Nagpaul
(74) *Attorney, Agent, or Firm* — Kenealy Valdya LLP

(57) ABSTRACT

A cell isolation instrument includes: a first container which has an opening in an upper portion; a filtration member which defines at least a part of a lower portion of the first container; an isolation member which is movably housed in the first container to collide with a tissue, thereby isolating cells; and a second container which houses the first container in a manner that the first container can be taken out.

4 Claims, 4 Drawing Sheets

CELL ISOLATION INSTRUMENT

BACKGROUND OF THE INVENTION

The present invention relates to a cell isolation instrument which is used in the field of clinics/research of regenerative medicine, or that of cell culture, and more particularly to a cell isolation instrument which is used for isolating cells from a tissue (body tissue) with a high survival rate.

There is a technique in which, in order to obtain isolated living cells, a tissue is minced with a sharp blade, and the minced tissue is subjected to an enzyme process with collagenase or the like to digest the extracellular matrix.

In the technique, procedures of the enzyme process and cell recovery must be repeatedly performed. Therefore, the technique requires labor and a long time period. The technique has a further problem in that the cell recovery rate is dispersed because of differences in the mincing process with using a blade and in the permeation rate in the enzyme process, etc.

JP-T-2007-505631 discloses an apparatus in which the mincing process and the enzyme process are automated. In a container disposed in the apparatus, a blade member which is rotatable about the central axis of the container, and a baffle which relatively provides a resistance to the movement of the blade member are placed. When a tissue from which isolated cells are to be obtained is loaded into the container and the blade member is rotated, the tissue in the state where the blade member bites into the tissue is rotated together, and collides with the baffle. The tissue is cut by the blade member because of the resistance provided by the baffle. When the rotation of the blade member is continued for a predetermined time period, the cutting is repeated, so that the tissue is minced. An enzyme treatment solution is previously loaded into the container, and therefore the enzyme process is performed in parallel.

In the configuration disclosed in JP-T-2007-505631, the mincing process and the enzyme process can be automated. In order to recover isolated cells, however, a cell suspension which is obtained as a result of the mincing process and the enzyme process must be taken out to the outside of the container, and then subjected to a filtering process. In realization of an automated system which stably recovers a large amount of isolated cells, the burden on the user must be mitigated, and influences of human procedures on the number and quality of isolated cells must be reduced. Therefore, it is necessary to reduce processes to be performed by the user, as far as possible. In the configuration disclosed in JP-T-2007-505631, however, the reduction of processes to be performed by the user is insufficient. Consequently, the configuration is inadequate for realizing an automated system.

SUMMARY

It is therefore an object of the invention to provide a cell isolation instrument in which processes to be performed by the user can be reduced as far as possible, and cells isolated from a tissue (body tissue) can be efficiently recovered.

In order to achieve the object, according to the invention, there is provided a cell isolation instrument comprising: a first container which has an opening in an upper portion; a filtration member which defines at least a part of a lower portion of the first container; an isolation member which is movably housed in the first container to collide with a tissue, thereby isolating cells; and a second container which houses the first container in a manner that the first container can be taken out.

The isolation member may include: a blade member; and a shaft member which rotatably supports the blade member in the first container. An upper end portion of the shaft member may be connectable to a cell isolation apparatus which rotates the shaft member.

The cell isolation instrument may further comprise a lid member which is fitted to the first container to close the opening. A through hole through which the shaft member is passed may be formed in the lid member, and at least a part of a portion, which is located below the lid member, of the shaft member may be larger in diameter than the through hole.

The lid member may include: a first lid member in which a first through hole through which the shaft member is passed, and at least one opening are formed; and a second lid member in which a second through hole through which the shaft member is passed, and which covers the at least one opening of the first lid member above the first lid member.

A groove may be formed in at least one of an outer wall of the first container and an inner wall of the second container.

In a state where the first container is housed in the second container, an upper end portion of the second container may be positioned above an upper end portion of the first container.

DETAILED DESCRIPTION OF EMBODIMENTS

Hereinafter, an embodiment of the invention will be described in detail with reference to the accompanying drawings.

Figure 1:
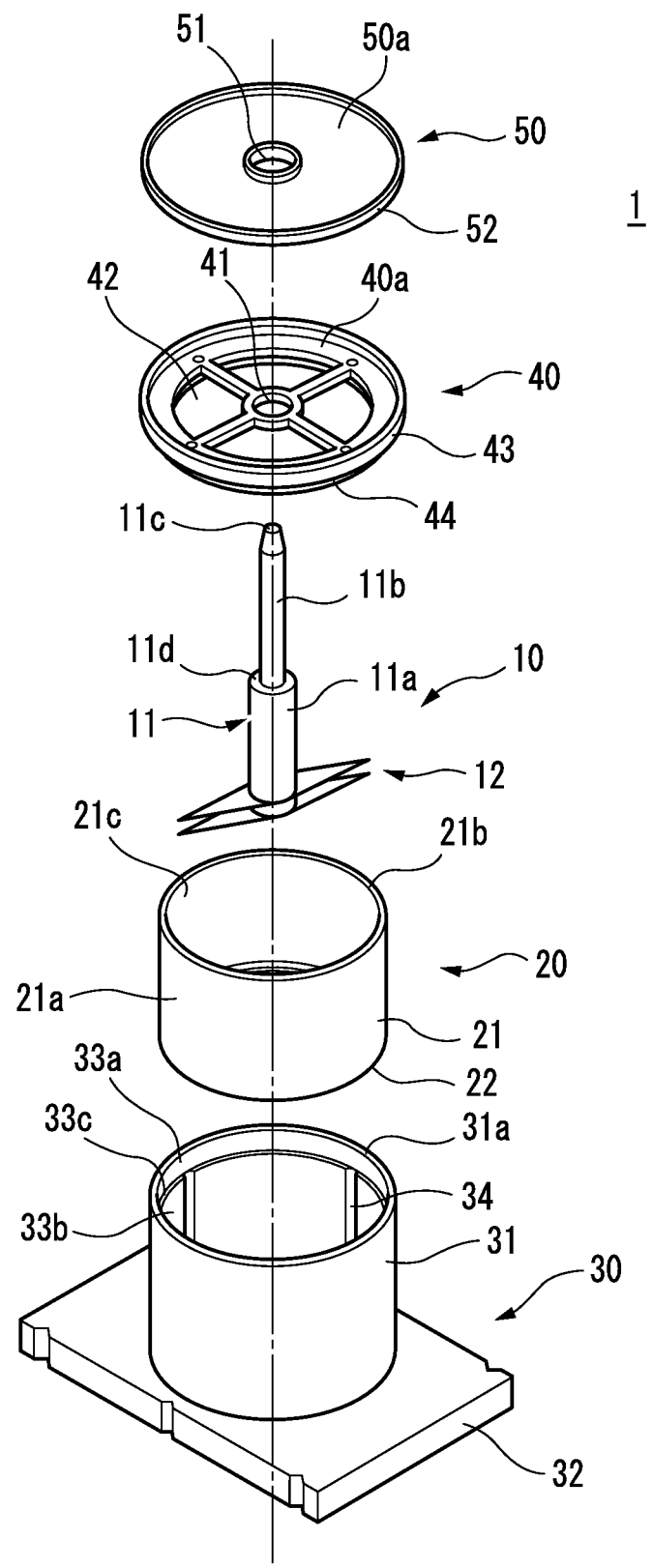
FIG. 1 is an exploded perspective view showing a cell isolation instrument of an embodiment of the invention.

FIG. 1 shows a state where a cell isolation instrument 1 of an embodiment of the invention is disassembled. The cell isolation instrument 1 includes an isolation member 10, an inner container (first container) 20, an outer container (second container) 30, an inner lid (lid member, first lid member) 40, and an outer lid (lid member, second lid member) 50. These components are formed by a material (such as a resin) which has resistance to ethylene oxide gas sterilization.

The isolation member 10 includes a shaft member 11 and a plurality of blade members 12. The shaft member 11 includes a large-diameter portion 11a, a small-diameter portion 11b, and a connecting portion 11c. The blade members 12 are supported by the lower end of the large-diameter portion 11a. The diameter of the small-diameter portion 11b is smaller than that of the large-diameter portion 11a, and a step 11d is formed in the interface between the large-diameter portion 11a and the small-diameter portion 11b. The connecting portion 11c is disposed in the upper end of the small-diameter portion 11b, and configured as a portion which is to be connected to a cell isolation apparatus 60 that will be described later.

The inner container 20 includes a body unit 21 and a filter (filtration member) 22. The body unit 21 is a cylindrical member which is opened in upper and lower portions. The filter 22 is formed by a material which is noncytotoxic. In the embodiment, nylon mesh having openings of 50 μm is used as the filter 22. The filter 22 is adhered or welded to the body unit 21 so as to cover the whole lower opening of the body unit 21.

The outer container 30 includes a body unit 31 and a pedestal portion 32. The body unit 31 is a cylindrical member which is opened in an upper portion. The inner side of the body unit 31 includes a first inner wall 33a and a second inner wall 33b. In the second inner wall 33b, a plurality of grooves 34 are formed at regular intervals in the circumferential direction of the body unit 31.

In an upper end portion of the body unit 31, the first inner wall 33a has a first inner diameter. The second inner wall 33b has a second inner diameter which is smaller than the first inner diameter, and which is larger than the outer diameter of the body unit 21 of the inner container 20. An inner step 33c is defined in the interface between the first inner wall 33a and the second inner wall 33b. The second inner wall 33b is continuous from the inner step 33c to a lower end portion of the body unit 31.

Figure 2:
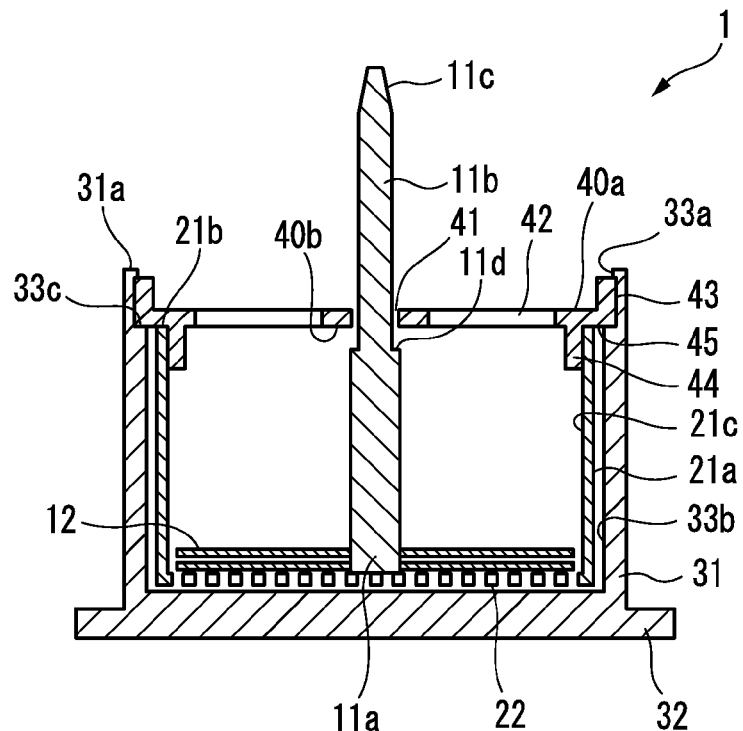
FIG. 2 is a longitudinal sectional view showing a state where the cell isolation instrument of FIG. 1 is in the course of assembling.

The inner lid 40 is a disk-like member which has an upper surface 40a and a lower surface 40b (see FIG. 2). A through hole (trough hole, first through hole) 41 through which the upper surface 40a and the lower surface 40b communicate with each other is formed in a center portion of the inner lid 40. A plurality of openings 42 through which the upper surface 40a and the lower surface 40b communicate with each other are formed so as to surround the through hole 41. The inner diameter of the through hole 41 is larger than the outer diameter of the small-diameter portion 11b of the shaft member 11 of the isolation member 10, and smaller than that of the large-diameter portion 11a.

The outer diameter of the inner lid 40 is approximately equal to the inner diameter (first inner diameter) of the first inner wall 33a of the body unit 31 of the outer container 30. An annular upper fitting wall 43 is formed in a circumferential portion of the upper surface 40a. An annular lower fitting wall 44 is formed slightly inside a circumferential portion of the lower surface 40b, and a step 45 is defined outside the wall (see FIG. 2). The outer diameter of the lower fitting wall 44 is approximately equal to the inner diameter of the body unit 21 of the inner container 20.

Figure 3:
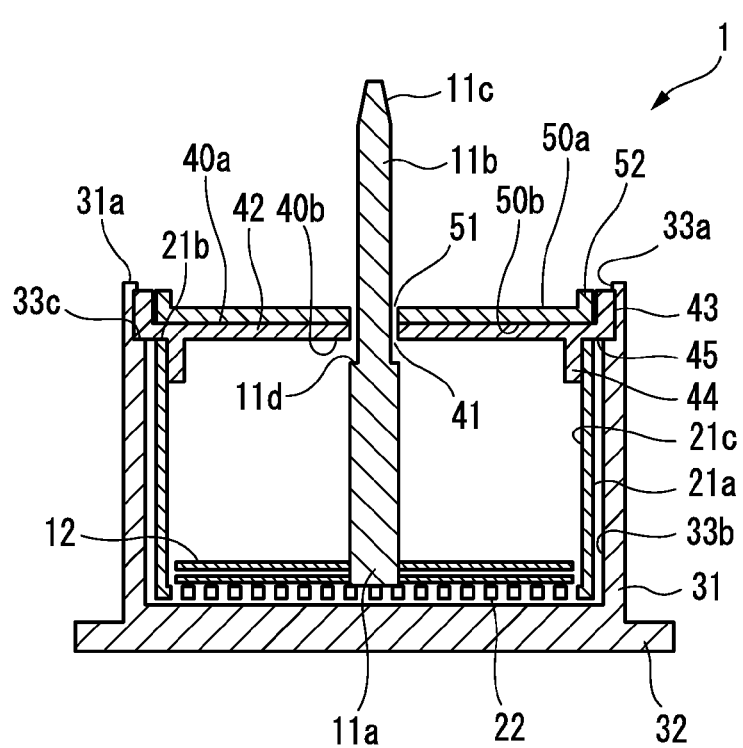
FIG. 3 is a longitudinal sectional view showing a state where the cell isolation instrument of FIG. 1 is assembled.

The outer lid 50 is a disk-like member which has an upper surface 50a and a lower surface 50b (see FIG. 3). A through hole (trough hole, second through hole) 51 through which the upper surface 50a and the lower surface 50b communicate with each other is formed in a center portion of the outer lid 50. The inner diameter of the through hole 51 is larger than the outer diameter of the small-diameter portion 11b of the shaft member 11 of the isolation member 10. The outer diameter of the outer lid 50 is approximately equal to the inner diameter of the upper fitting wall 43 of the inner lid 40. An annular fitting wall 52 is disposed in a circumferential portion of the upper surface 50a.

Next, a method of assembling the cell isolation instrument of the embodiment, and a part of steps of a cell isolating process will be described with reference to FIGS. 2 and 3.

First, the inner container 20 is housed in the outer container 30 in a posture in which the filter 22 is downward directed. At this time, the outer wall 21a of the inner container 20 is opposed to the second inner wall 33b of the outer container 30 through a small gap. The upper end surface 21b of the body unit 21 is flush with the inner step 33c of the body unit 31.

In the state where the inner container 20 is housed in the outer container 30, the upper end surface (upper end portion) 31a of the outer container 30 is positioned above the upper end surface (upper end portion) 21b of the inner container 20.

Next, the isolation member 10 is housed in the inner container 20. At this time, a lower end portion of the shaft member 11 is placed on the filer 22.

Then, the inner lid 40 is attached so that the small-diameter portion 11b of the shaft member 11 of the isolation member 10 is passed through the through hole 41. At this time, the step 45 of the inner lid 40 is placed on the upper end surface 21b of the inner container 20, and the inner step 33c of the outer container 30. Furthermore, the lower fitting wall 44 of the inner lid 40 is fitted to an inner wall 21c of the inner container 20, and the upper fitting wall 43 is fitted to the first inner wall 33a of the outer container 30.

In the state shown in FIG. 2, a predetermined amount of enzyme treatment solution which is previously heated to the activation temperature is poured into the inner container 20 through the openings 42. A tissue which is extracted from a living body for the purpose of isolation of cells is loaded similarly through the openings 42 into the inner container 20.

Next, the outer lid 50 is attached so that the small-diameter portion 11b of the shaft member 11 of the isolation member 10 is passed through the through hole 51. At this time, the lower surface 50b of the outer lid 50 covers the openings 42 of the inner lid 40 to prevent foreign substances from entering the inner container 20 in the subsequent steps. The fitting wall 52 of the outer lid 50 is fitted to the inner side of the upper fitting wall 43 of the inner lid 40. FIG. 3 shows this state. A small gap is formed between the small-diameter portion 11b of the shaft member 11 and the through holes 41, 51.

Figure 4:
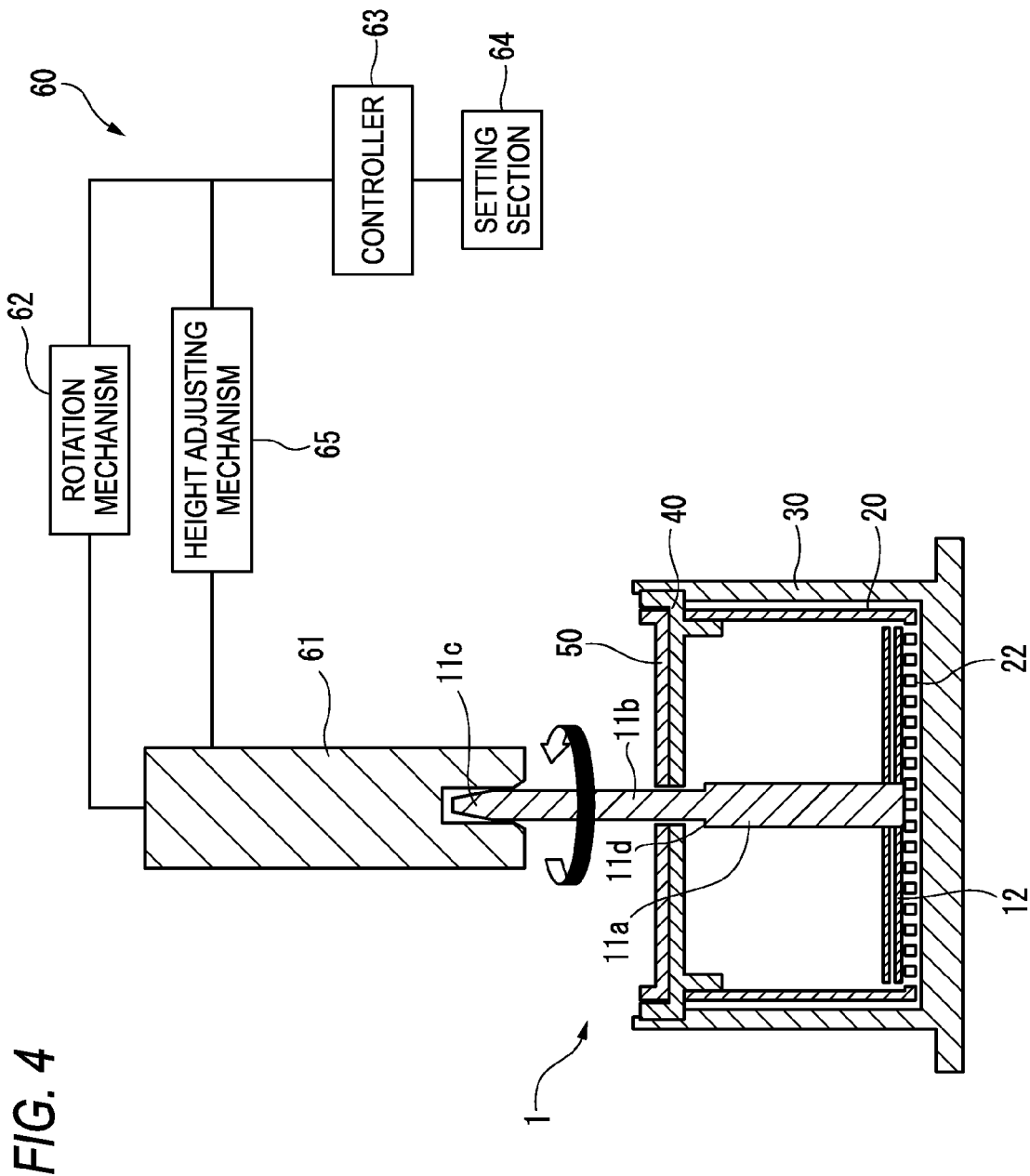
FIG. 4 is a longitudinal sectional view showing a state where the cell isolation instrument of FIG. 1 is connected to a cell isolation apparatus.

As a result of the above-described steps, the cell isolation instrument 1 which accommodates the tissue and the enzyme treatment solution is placed on a stage (not shown) disposed in the cell isolation apparatus 60. As shown in FIG. 4, the cell isolation apparatus 60 includes a bearing member 61, a rotation mechanism 62, a controller 63, a setting section 64, and a height adjusting mechanism 65. In accordance with stirring conditions (the number of rotations, the rotation method, the duration time, and the like) which are set by the user through the setting section 64, the controller 63 controls the rotation mechanism 62 to rotate the bearing member 61.

In accordance with user instructions or in an automatic manner, the controller 63 controls the height adjusting mechanism 65 to vertically move at least one of the stage and the bearing member 61. This operation causes the connecting portion 11c of the shaft member 11 of the isolation member 10 to be connected to the bearing member 61. The isolation member 10 is fixed to a position where the lower end portion of the shaft member 11 is separated from the filter 22, and the step 11d of the shaft member 11 is not contacted with the lower surface 40b of the inner lid 40. The isolation member 10 is supported by the bearing member 61, so that the blade members 12 can be rotated in the inner container 20 with the rotation of the bearing member 61. FIG. 4 shows this state.

When the user sets the stirring conditions through the setting section 64 and inputs instructions for starting the process, the controller 63 controls the rotation mechanism 62 in accordance with the preset stirring conditions so that the blade members 12 are rotated in the inner container 20 through the bearing member 61. As a result, the mincing process and the enzyme process are automatically applied on the tissue.

There is a possibility that, when isolated cells are immersed in the enzyme treatment solution in the outer container 30 for a long term, the cells may be damaged. sometimes, therefore, the enzyme process is performed divisionally in a plurality of steps. Specifically, the inner container 20 is lifted, and the filtered cell suspension is once acquired. Thereafter, a new enzyme treatment solution is poured into the outer container 30, and the inner container 20 is lowered, whereby the isolating process and the enzyme process are again performed. In a related art, these works must be manually performed. According to the configuration of the embodiment, when the user sets a plurality of enzyme processes through the setting section 64, the desired enzyme processes can be executed automatically and at adequate timings.

During the stirring operation, the enzyme treatment solution may enter the gap between the inner container 20 and the outer container 30. However, the grooves 34 which are formed in the second inner wall 33b of the outer container 30 function as an escape route for the entering enzyme treatment solution. Therefore, a situation where the entering enzyme treatment solution is caused to rise through the gap by the capillary force, and the solution leaks to the outside of the inner container 20 can be prevented from occurring. Even when the enzyme treatment solution leaks out, the enzyme treatment solution remains on the upper surface 50a of the outer lid 50 because the upper end surface 31a of the outer container 30 is positioned above the upper end surface 21b of the inner container 20, and therefore the solution does not leak to the outer side surface of the outer container 30.

Figure 5:
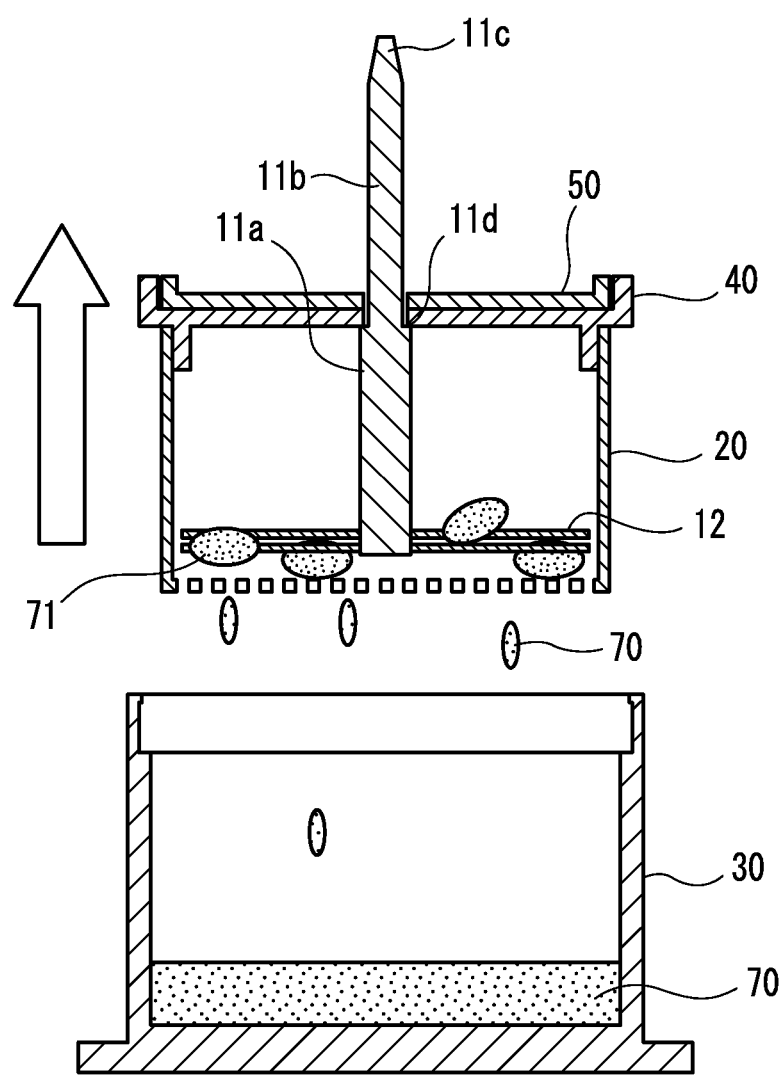
FIG. 5 is a longitudinal sectional view showing a state where a filtered cell suspension is recovered by using the cell isolation instrument of FIG. 1.

When the stirring operation is ended, a solution in which minced tissue pieces and isolated cells are suspended in the enzyme treatment solution is obtained in the cell isolation instrument 1. Next, a step of recovering the isolated cells from the solution will be described with reference to FIG. 5.

First, the connection of the cell isolation instrument 1 and the cell isolation apparatus 60 is cancelled, and the cell isolation instrument 1 is taken out from the cell isolation apparatus 60. While holding the outer container 30, the shaft member 11 of the isolation member 10 is gripped and lifted upward, and then the step 11d abuts against the lower surface 40b of the inner lid 40 because the large-diameter portion 11a of the shaft member 11 is larger in diameter than the through hole 41 of the inner lid 40. When the shaft member 11 is further upward lifted, the inner container 20 can be lifted upward while the inner lid 40 remains to be fitted into the inner container 20.

At this time, unwanted tissue pieces 71 contained in the solution cannot be passed through the filter 22 because they are larger than the mesh openings of the filter 22, and remain in the inner container 20. By contrast, the cell suspension 70 containing isolated cells which are smaller than the mesh openings of the filter 22 are passed through the filter 22 to flow down into the outer container 30.

According to the configuration of the embodiment, namely, the cell suspension 70 containing isolated cells can be recovered easily and surely into the outer container 30, simply by the simple operation of lifting up the inner container 20 to be taken out from the outer container 30. Therefore, the efficiency of the step of recovering isolated cells can be remarkably improved.

The embodiment has been described in order to facilitate understanding of the invention, and is not intended to limit the invention. It is a matter of course that the invention may be changed or improved without departing the spirit thereof, and includes equivalent embodiments.

The filter 22 is not always required to cover the whole opening in the lower portion of the inner container 20. It is required that the filter 22 forms at least a part of the lower portion of the inner container 20 in a range where the recovery of isolated cells by filtration is not disturbed.

The isolation member 10 is not always required to be configured by the shaft member 11 which rotatably supports the blade members 12. Various other configurations such as a configuration where a stirrer is used may be employed as far as a collision occurs on a tissue and cells can be isolated.

The inner lid 40 is not always necessary. In the case where the inner lid is not disposed, the inner diameter of the through hole 51 of the outer lid 50 is made smaller than that of the large-diameter portion 11a of the shaft member 11 of the isolation member 10 because, when the shaft member 11 is lifted up, the step 11d must abut against the lower surface 50b of the outer lid 50.

The step of recovering isolated cells maybe automated. For example, a configuration maybe employed where a structure for holding the outer container 30 is disposed on the stage of the cell isolation apparatus 60, and, after the stirring operation, the height adjusting mechanism 65 is caused by the controller 63 to perform an operation of lifting the bearing member 61. The shaft member 11 in the state where it is connected to the bearing member 61 is lifted up, and the inner container 20 can be taken out from the outer container 30.

It is not always necessary to form the plurality of openings 42 in the inner lid 40. The number and size of at least one opening 42 can be adequately determined within a range where the workability of the operation of loading the enzyme treatment solution and the tissue is not impaired.

The grooves 34 are not always required to be formed in the second inner wall 33b of the outer container 30. Even when the grooves are formed in the outer wall 21a of the inner container 20 opposed to the second inner wall 33b, it is possible to prevent the enzyme treatment solution from leaking out. Alternatively, the grooves may be formed in both the second inner wall 33b and the outer wall 21a.

According to an aspect of the invention, the filtered cell suspension is allowed to be recovered into the second container, simply by taking out the first container from the second container.

According to an aspect of the invention, the rotation of the shaft member can be controlled on the side of the cell isolation apparatus, and a cell isolation step including the process of mincing the tissue, and the enzyme process can be easily automated. When living cells are to be recovered, fine adjustment is necessary because characteristics such as the hardness and the size are different depending on tissues. In the invention, however, it is requested only to adjust the rotation speed and time, kind, and the like of the blade member in accordance with the tissue to be recovered, and various cells can be recovered in the living state by the same cell isolation instrument.

According to an aspect of the invention, the first container can be taken out simply by lifting the shaft member, and steps until the step of recovering the filtered cell suspension can be easily automated. Furthermore, the works of lifting the first container to acquire the cell suspension, then pouring a new enzyme solution into the second container, again housing the first container in the second container, and performing the enzyme process a plurality of times can be easily automatized. Therefore, damage to the isolated cells caused by long-term immersion of the cells in the enzyme solution can be mitigated.

According to an aspect of the invention, the tissue and the enzyme treatment solution are loaded into the first container through the minimum necessary opening, and thereafter the opening is covered by the second lid member. Therefore, it is possible to prevent foreign substances from entering the device during the cell isolating process and the recovering process.

According to an aspect of the invention, the enzyme treatment solution and cell suspension which enter the gap between the first and second containers are guided to the groove. Therefore, it is possible to prevent liquids from leaking to the outside of the first container.

According to an aspect of the invention, even when the enzyme treatment solution and the cell suspension leak from the first container, they cannot override the upper end of the second container. Therefore, leakage to the outside of the second container, i.e., the outside of the cell isolation instrument can be prevented from occurring.

What is claimed is:

1. A cell isolation instrument comprising:
a first container which has an opening in an upper portion;
a filtration member which defines at least a part of a lower portion of the first container;
an isolation member which is movably housed in the first container to collide with a tissue, thereby isolating cells;
a second container which houses the first container in a manner that the first container can be taken out, and
a lid member which is fitted to the first container to close the opening,
wherein the isolation member includes:
a blade member; and
a shaft member which rotatably supports the blade member in the first container, and
wherein an upper end portion of the shaft member is connectable to a cell isolation apparatus which rotates the shaft member, and
wherein a through hole through which the shaft member is passed is formed in the lid member, and at least a part of a portion, which is located below the lid member, of the shaft member is larger in diameter than the through hole.

2. The cell isolation instrument according to claim 1, wherein the lid member includes:
a first lid member in which a first through hole through which the shaft member is passed, and at least one opening are formed; and
a second lid member in which a second through hole through which the shaft member is passed, and which covers the at least one opening of the first lid member above the first lid member.

3. The cell isolation instrument according to claim 1, wherein a groove is formed in at least one of an outer wall of the first container and an inner wall of the second container.

4. The cell isolation instrument according to claim 1, wherein, in a state where the first container is housed in the second container, an upper end portion of the second container is positioned above an upper end portion of the first container.

* * * * *